(12) United States Patent
Esch

(10) Patent No.: US 9,821,309 B2
(45) Date of Patent: Nov. 21, 2017

(54) POROUS MEMBRANE APPARATUS, METHOD, AND APPLICATIONS

(71) Applicant: CORNELL UNIVERSITY, Ithaca, NY (US)

(72) Inventor: Mandy B. Esch, Ithaca, NY (US)

(73) Assignee: CORNELL UNIVERSITY, Ithaca, NY (US)

(*) Notice: Subject to any disclaimer, the term of this patent is extended or adjusted under 35 U.S.C. 154(b) by 145 days.

(21) Appl. No.: 14/409,617

(22) PCT Filed: Jul. 3, 2013

(86) PCT No.: PCT/US2013/049255
§ 371 (c)(1),
(2) Date: Dec. 19, 2014

(87) PCT Pub. No.: WO2014/008358
PCT Pub. Date: Jan. 9, 2014

(65) Prior Publication Data
US 2015/0174573 A1    Jun. 25, 2015

Related U.S. Application Data

(60) Provisional application No. 61/668,224, filed on Jul. 5, 2012.

(51) Int. Cl.
| | |
|---|---|
| *G03F 7/20* | (2006.01) |
| *B01L 3/00* | (2006.01) |
| *C12M 3/06* | (2006.01) |
| *C12M 1/12* | (2006.01) |

(52) U.S. Cl.
CPC ........ *B01L 3/502707* (2013.01); *C12M 23/16* (2013.01); *C12M 25/02* (2013.01); *C12M 25/14* (2013.01); *G03F 7/2022* (2013.01); *B01L 2200/0647* (2013.01); *B01L 2200/10* (2013.01); *B01L 2200/12* (2013.01)

(58) Field of Classification Search
CPC ..... B41L 2/1631; B41L 2/1621; B41J 2/1631; B41J 2/1621; B01L 3/502707; B01L 3/502; B01L 3/50; G03F 7/2022; G03F 7/20; C12M 23/16; C12M 23/02; C12M 23/00
USPC .................... 435/289.1, 283.1; 430/320, 269
See application file for complete search history.

(56) References Cited

U.S. PATENT DOCUMENTS

| | | | |
|---|---|---|---|
| 6,752,966 B1 | 6/2004 | Chazan | |
| 6,790,599 B1 | 9/2004 | Madou | |
| 2005/0064581 A1 | 3/2005 | Manalis et al. | |
| 2007/0048727 A1* | 3/2007 | Shuler | C12M 21/08 435/1.2 |
| 2007/0092411 A1 | 4/2007 | Leach et al. | |
| 2008/0107878 A1* | 5/2008 | Irving | G03F 7/2014 428/209 |
| 2010/0119711 A1* | 5/2010 | Cady | B01L 3/0248 427/256 |
| 2010/0221463 A1 | 9/2010 | Zine-El-Abidine et al. | |
| 2011/0203936 A1* | 8/2011 | Kulinsky | C25D 5/02 205/95 |

OTHER PUBLICATIONS

International Search Report Form PCT/ISA/210, International Application No. PCT/US2013/049255, International Filing Date Jul. 3, 2013, dated Oct. 13, 2011, pp. 1-3.

* cited by examiner

*Primary Examiner* — Christine T Mui
(74) *Attorney, Agent, or Firm* — Bond, Schoeneck & King, PLLC; William Greener; Blaine Bettinger

(57) ABSTRACT

Microporous membranes formed in a microfluidic device, and methods of manufacture. A method comprises the steps of etching a plurality of pillars in a microfluidic chamber, applying a first polymer material layer, applying a photoresist layer, exposing the photoresist layer to radiation to cross-link it to the microfluidic chamber, masking the photoresist layer with a porous mask, exposing the top layer of the masked photoresist layer to radiation to form a porous membrane layer of cross-linked photoresist material, removing the non-exposed photoresist material from under the porous membrane layer, drying the porous membrane layer, and removing the first polymer material from under the porous membrane layer.

14 Claims, 19 Drawing Sheets

FIG. 7C
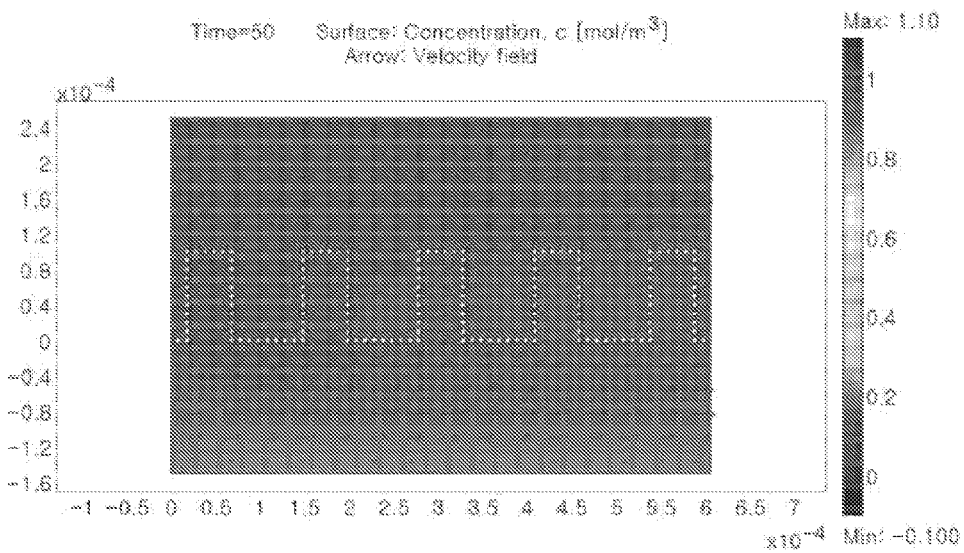
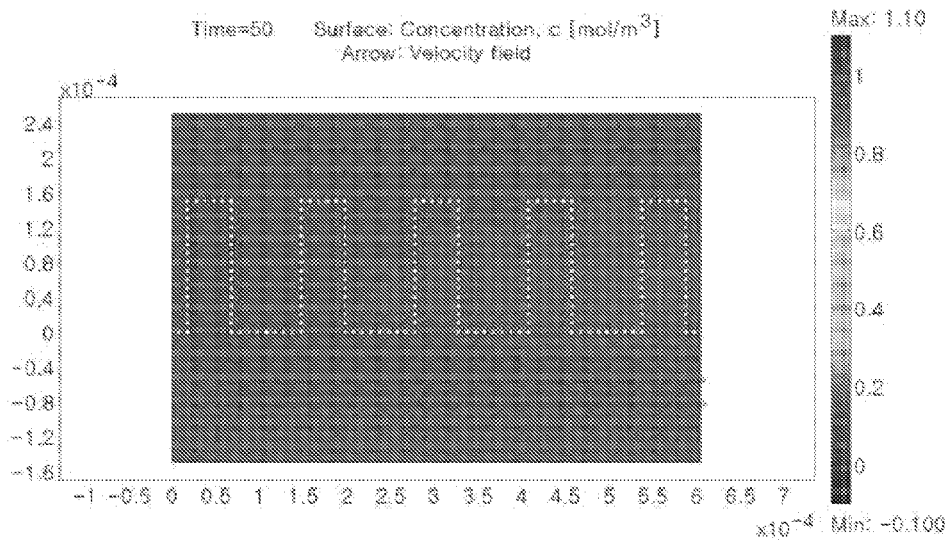
FIG. 7D

Flat Membrane Fabrication on top of an Existing Microfluidic Chamber

Microfluidic Chamber and Flat Membrane Fabrication

POROUS MEMBRANE APPARATUS, METHOD, AND APPLICATIONS

CROSS-REFERENCE TO RELATED APPLICATIONS

This application is a U.S. national phase filing of PCT/US13/49255, filed Jul. 3, 2013 and claims the benefit thereof, which claims priority to U.S. Provisional Patent Application Ser. No. 61/668,224, filed Jul. 5, 2012 and entitled "Three Dimensional Porous Membrane Apparatus, Method, and Applications," the entire disclosure of which is incorporated herein by reference.

GOVERNMENT FUNDING

This invention was made with Government support under Grant Number CERL-W9132T awarded by the Army Corps of Engineers and CBET-1106153 awarded by the NSF. The United States Government has certain rights in the invention.

BACKGROUND OF THE INVENTION

1. Field of the Invention

The present invention relates to microfluidic cell culture systems and, more specifically, to microfluidic cell culture systems comprising microporous, polymeric, flat or three-dimensional membranes that can mimic barrier tissue. These membranes can be incorporated into, and fabricated simultaneously with, a microfluidic chamber. Accordingly, the fabrication allows for leak-free, direct attachment of the microporous membranes to the walls of the microfluidic chamber.

2. Description of the Related Art

Microfluidic cell culture systems that contain several compartments for the culture of multiple tissues such as the gastrointestinal tract epithelium, liver, kidney and tumor tissues are currently being developed for the purpose of studying the collective response of multiple organs to new drugs under near physiologic conditions. Low bioavailability of drugs at the target organ has been cited as one of the major reasons for the failure of newly developed drugs in clinical trials. Drug testing systems that contain models of barrier tissues such as the gastrointestinal tract epithelium and the lung epithelium are invaluable for correctly predicting the bioavailability of newly developed drugs early in the drug development process.

Microfluidic tissue analogs of barrier tissues replicate the physiologic aspects of these tissues with more authenticity than static models that are currently being used. In microfluidic systems the ratios of in vivo masses or volumes of organs can be recreated on chip, and physiologic fluid residence times in each organ can be achieved. Moreover, metabolites produced in one tissue can travel to other organ compartments and affect the tissues cultured there. Such devices have the potential to improve the drug screening process significantly, because they recreate parts of the human metabolism.

A few microfluidic in vitro analogs of barrier tissues have been developed so far, but none of these models recreate the three dimensional villi structure that increases the absorptive area in the small intestine. The existing models also do not combine other tissues with the developed models in one system. The developed devices may contain semipermeable membranes that were sandwiched between two microfluidic chambers. The membranes provide a surface for cell growth and at the same time they separate the chambers that contain differing concentrations of compounds that are used in the study. The pores in the membranes allow for the transport of molecules across the cell layer. Using semipermeable membranes, the development of in vitro cell culture analogs of tissues of the lung, the gastrointestinal tract and the kidney has been achieved. However, sandwiching membranes between two existing tissue chambers is challenging. It is not always possible to assemble such systems so that they are leak-free.

Because sheets of membranes are difficult to integrate with microfluidic systems, multi-organ cell culture devices are limited in regards to the barrier tissues they contain. As a consequence the microfluidic systems that connect the basolateral chamber of a barrier tissue model with another tissue chamber utilize off-chip modules that are connected to on-chip components. For example, others have developed off-chip chambers that utilize transwell membrane inserts for the culture of intestinal epithelial cells under fluidic conditions. Both systems have been used in combination with liver cell chambers to create in vitro models of intestinal absorption and first pass metabolism of drugs. Both systems cannot scale the surface area of the intestinal epithelium to approximate the in vivo ratio of epithelial surface area to the mass and volume of liver tissue because the sizes of transwell membranes that are used within the modules are fixed. Membranes that are fabricated directly on top of microfluidic chambers and that can be directly attached to the chamber sidewalls could be scaled appropriately and would not be prone to leaking.

Porous silicon nitride membranes address one of these issues because they can span microfluidic compartments of varying sizes and have been used for the culture of endothelial cells in an effort to recreate part of the blood brain barrier in vitro. However, silicon nitride membranes are typically patterned at the front side of silicon wafers and released by etching from the backside. Integrating these membranes with microfluidic systems requires one or two bonding steps to create closed fluidic chambers. This process is not straightforward if the desired chamber depth is less than the thickness of the silicon substrate (~500 µm), which is typically the case in "body-on-a-chip" devices. Flexibility in choosing chamber dimensions such as the chamber depth is necessary to be able to adjust fluid residence times within individual organ compartments. Typical values for chamber depths range from 20-200 µm.

In addition, both commercially available membranes and microfabricated membranes are typically flat and do not recreate the three-dimensional aspects of tissues such as the macro villi of the gastrointestinal tract epithelium. The gastrointestinal tract epithelium contains both micro and macro villi that increase the absorptive area of the intestine. Conventional models of the gastrointestinal tract such as Caco-2 monolayers do not provide three-dimensional surfaces that take the geometric character of the tissue into account. Mimicking the tissue organization of the intestinal epithelium authentically requires microscale three-dimensional semipermeable membranes that act as cell culture surface and control mass transport.

Other prefabricated membranes also do not mimic the appropriate three-dimensional structure of tissue, (that means they are not three-dimensional) because they either lack the required rigidity to control a 3-D three-dimensional and/or lack sufficient porosity. Any three-dimensional cell culture scaffold to date is not a membrane. They are based on alginate, basement membrane proteins, plastics or polymerizable compounds. Accordingly, access to the underside of the cell culture is not possible with these methods.

BRIEF SUMMARY OF THE INVENTION

According to an aspect, a method of producing a porous membrane in a microfluidic chamber comprising: (i) applying a photoresist material onto the microfluidic chamber to form a photoresist material layer, wherein the microfluidic chamber comprises a plurality of pillars; (ii) exposing a peripheral portion of the photoresist material layer to radiation, wherein exposing the photoresist material layer to radiation cross-links the exposed peripheral portion to the microfluidic chamber; (iii) masking, using a mask comprising a plurality of pores formed therein, the photoresist material layer; (iv) exposing a top layer of the masked photoresist material layer to radiation to form a porous membrane layer of cross-linked photoresist material; (v) removing the non-exposed photoresist material from under the porous membrane layer; (vi) drying the porous membrane layer; and (vii) creating a space between a portion of the porous membrane layer and a portion of the microfluidic chamber.

According to another embodiment, the method further comprises the steps of: (i) etching a portion of the microfluidic chamber to create the plurality of pillars; and/or (ii) applying a first polymer material onto the etched microfluidic chamber to form a first polymer layer.

According to another aspect, the step of creating a space between a portion of the porous membrane layer and a portion of the microfluidic chamber comprises removing the first polymer material.

According to yet another aspect, the step of creating a space between a portion of the porous membrane layer and a portion of the microfluidic chamber comprises removing one or more of the plurality of pillars.

According to an embodiment, the photoresist material is SU-8. The first polymer material can be, for example, OMNICOAT™ polymer. According to another embodiment, the mask is a photolithography mask.

According to another aspect, the steps of applying the first polymer material onto the etched microfluidic chamber and applying the photoresist material comprise spin coating.

According to an embodiment, the step of removing the non-exposed photoresist material from under the porous membrane layer comprises incubating in photoresist material developer According to another aspect, the step of removing the first polymer material from under the porous membrane layer comprises incubating in a developer suitable to remove said first polymer material.

According to yet another aspect, the etching step comprises the steps of: (i) applying an initial photoresist material onto the microfluidic chamber to form an initial photoresist material layer; (ii) exposing the initial photoresist material layer to radiation in a predetermined pillar array pattern; (iii) etching the microfluidic chamber to create a plurality of pillars corresponding to the predetermined pillar array pattern formed in the exposed initial photoresist material layer; and (iv) removing all of the initial photoresist material. The initial photoresist material can be SC™ 1827.

According to another aspect, the method further comprises the steps of: (i) seeding the porous membrane layer with a plurality of cells; and (ii) incubating the seeded porous membrane layer under conditions suitable to promote growth of said seeded cells. The cells can be, for example, Caco-2 cells.

According to another embodiment is a method of producing a porous membrane in a microfluidic chamber, the method comprising the steps of: (i) applying a photoresist material onto the microfluidic chamber to form a photoresist material layer; (ii) exposing a peripheral portion of the photoresist material layer to radiation, wherein exposing the photoresist material layer to radiation cross-links the exposed peripheral portion to the microfluidic chamber; (iii) masking, using a mask comprising a plurality of pores formed therein, the photoresist material layer; (iv) exposing a top layer of the masked photoresist material layer to radiation to form a porous membrane layer of cross-linked photoresist material; and (v) removing the non-exposed photoresist material from under the porous membrane layer.

According to another aspect, the method further comprises, prior to the masking step, the step of exposing a central portion of the photoresist material layer to radiation, wherein a plurality of cross-linked support posts are created in said photoresist material layer.

According to yet another aspect, the method further comprises the steps of: (i) seeding the porous membrane layer with a plurality of cells; and (ii) incubating the seeded porous membrane layer under conditions suitable to promote growth of said seeded cells.

According to another aspect is a microfluidic device comprising: (i) a microporous membrane cross-linked at its periphery to a first portion of the microfluidic device, wherein the microporous membrane is fabricated from a photoresist material layer simultaneously with fabrication of the microfluidic device; (ii) a cavity defined on one side by a portion of the microporous three-dimensional membrane and on another side by a second portion of the microfluidic device; (iii) wherein the microporous membrane comprises a plurality of three-dimensional shapes extending outwardly from the cavity. According to another aspect, the photoresist material is SU-8.

According to another aspect, the microporous three-dimensional membrane is fabricated according to the following steps in order to fabricate the plurality of three-dimensional shapes extending outwardly from the cavity: (i) applying a photoresist material onto the microfluidic device to form a photoresist material layer, wherein the microfluidic device comprises a plurality of pillars; (ii) exposing a peripheral portion of the photoresist material layer to radiation, wherein exposing the photoresist material layer to radiation cross-links the exposed peripheral portion to the microfluidic device; (iii) masking, using a mask comprising a plurality of pores formed therein, the photoresist material layer; (iv) exposing a top layer of the masked photoresist material layer to radiation to form a porous membrane layer of cross-linked photoresist material; (v) removing the non-exposed photoresist material from under the porous membrane layer; (vi) drying the porous membrane layer; and (vii) creating a space between a portion of the porous membrane layer and a portion of the microfluidic device.

The details of one or more embodiments are described below and in the accompanying drawings. Other objects and advantages will in part be obvious, and in part appear hereinafter.

BRIEF DESCRIPTION OF THE SEVERAL VIEWS OF THE DRAWING(S)

The present invention will be more fully understood and appreciated by reading the following Detailed Description in conjunction with the accompanying drawings, in which:

FIG. 3A is a fluorescence microscopy image of Caco-2 cells immunostained for occluding, and FIG. 3B is a scanning electron microscopy image of Caco-2 cells and an underlying membrane;

Figure 4:
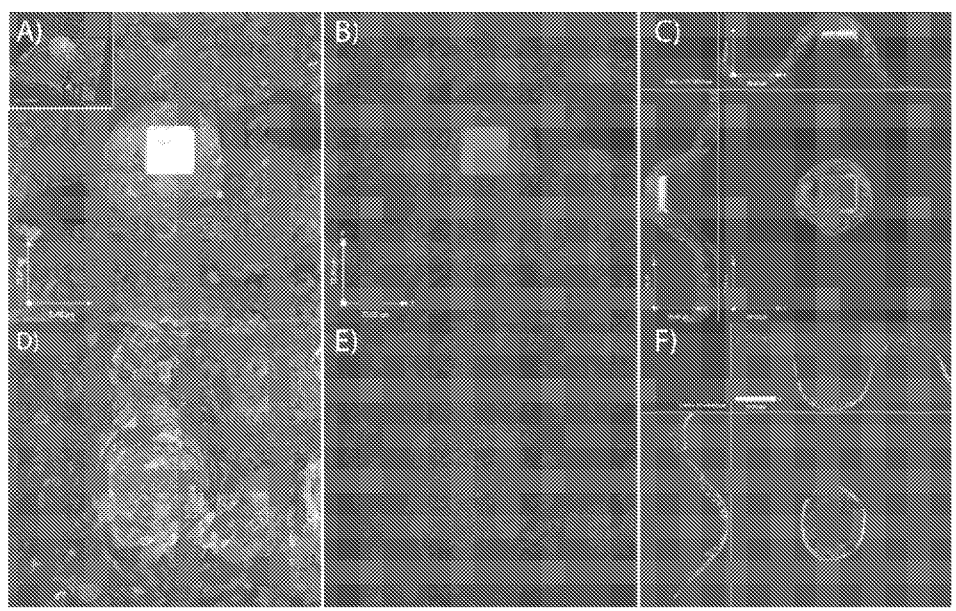
Figure 5:
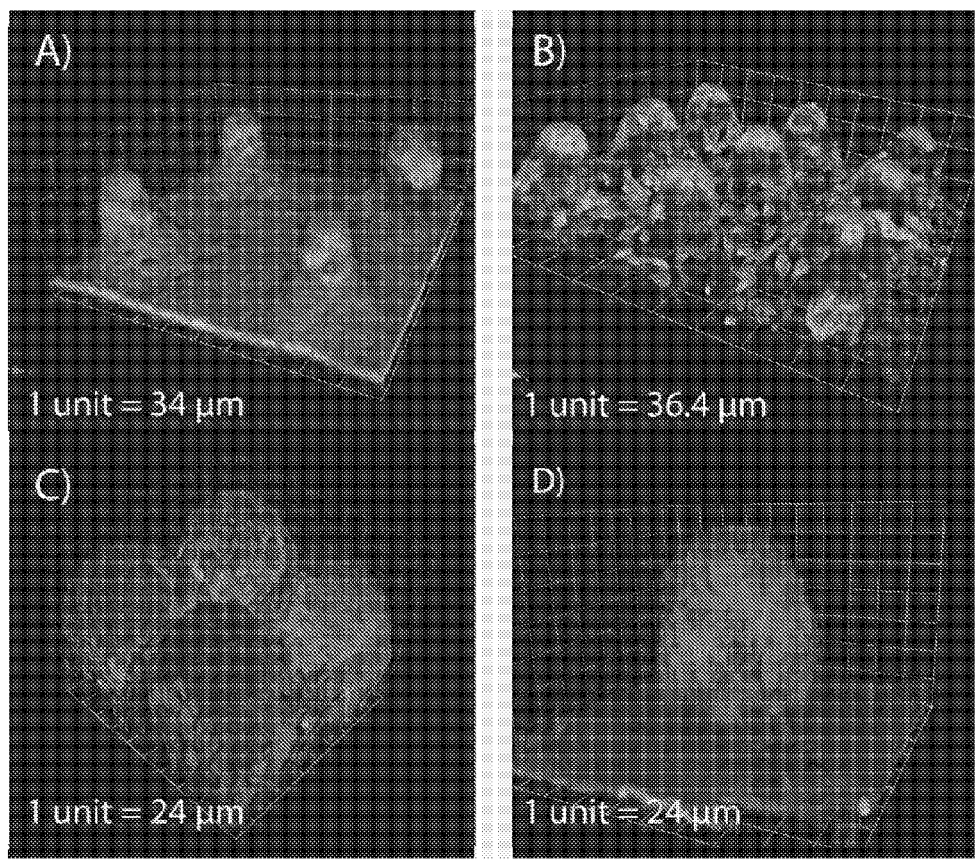
Figure 6:
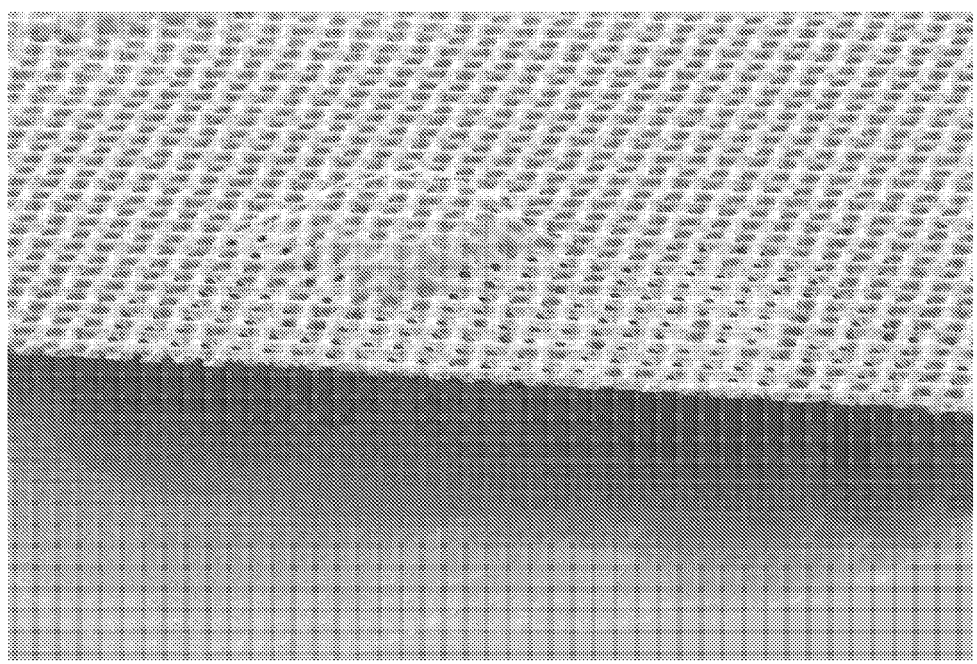
Figure 7A:
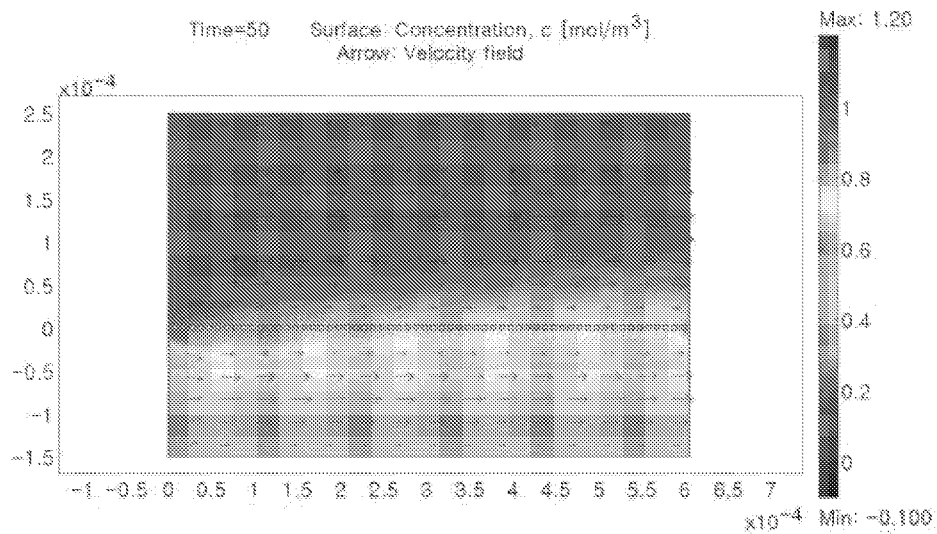
Figure 7B:
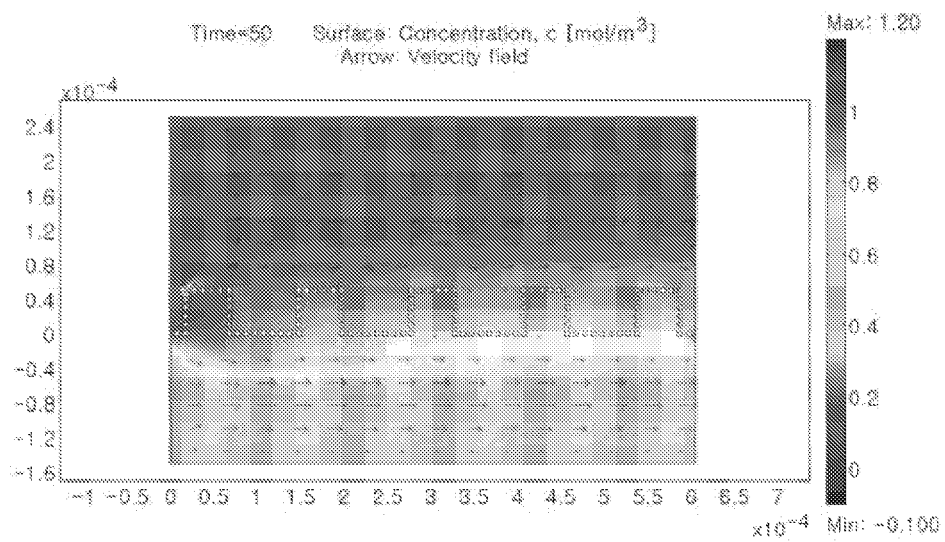
Figure 8:
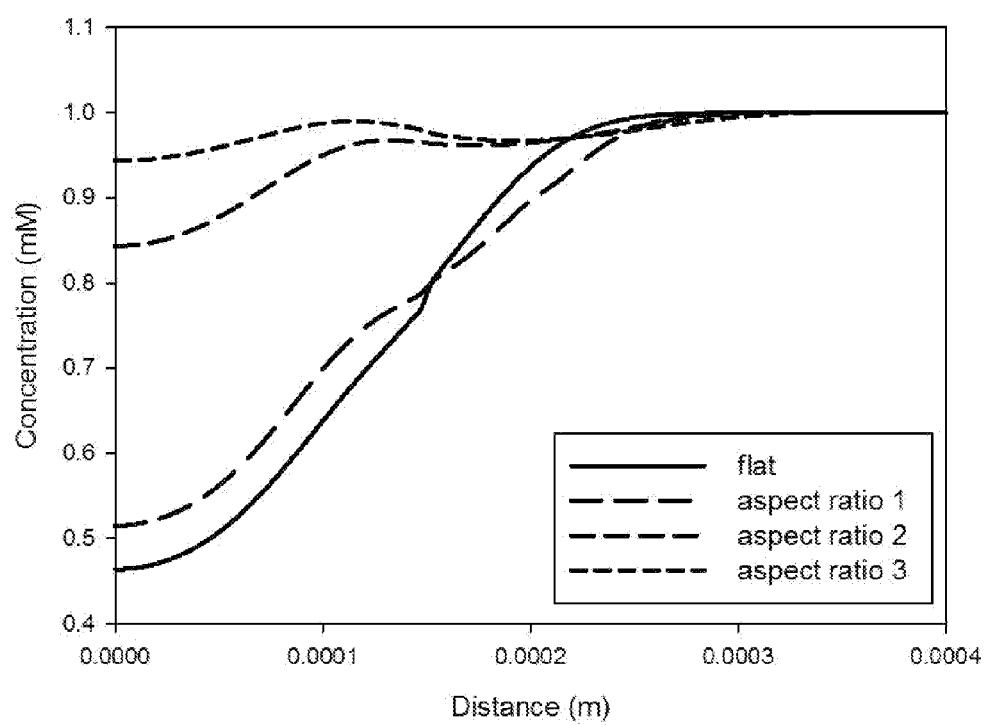
Figure 9A:
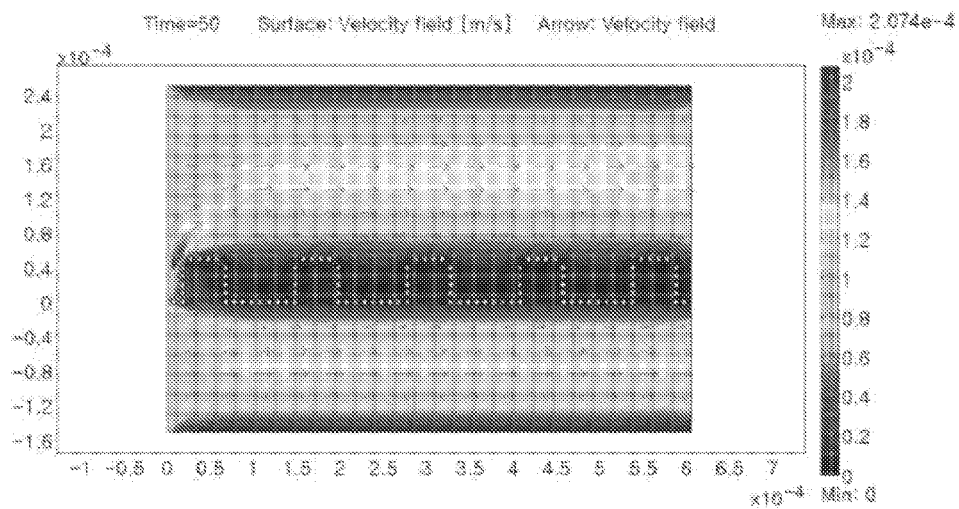
Figure 10:
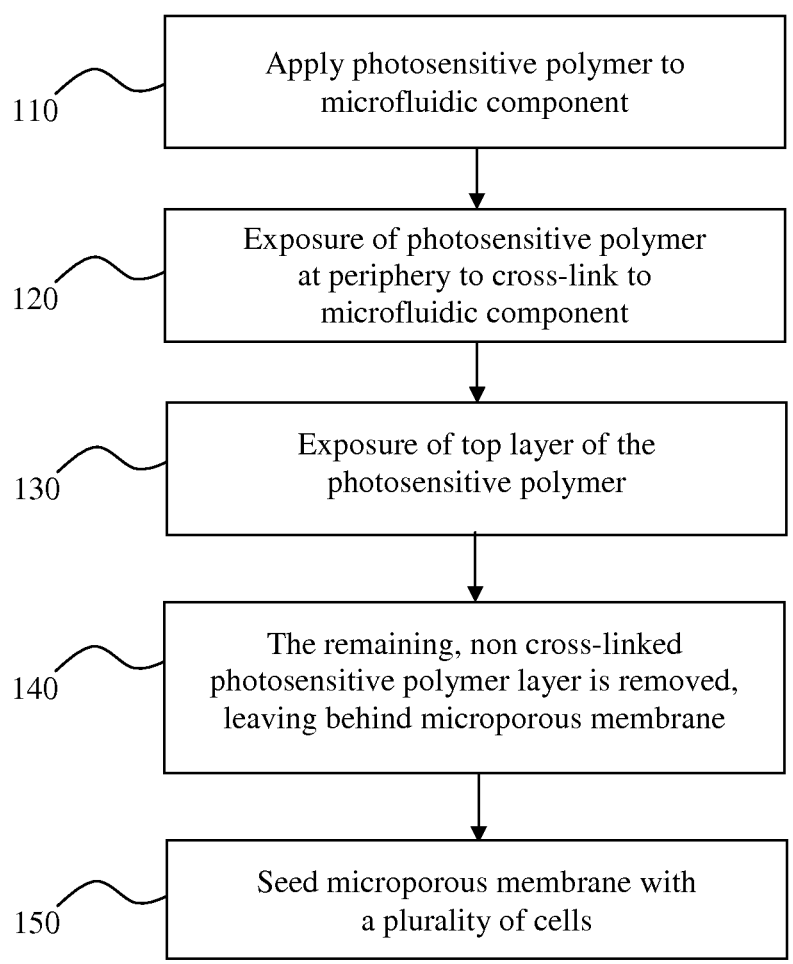
Figure 11:
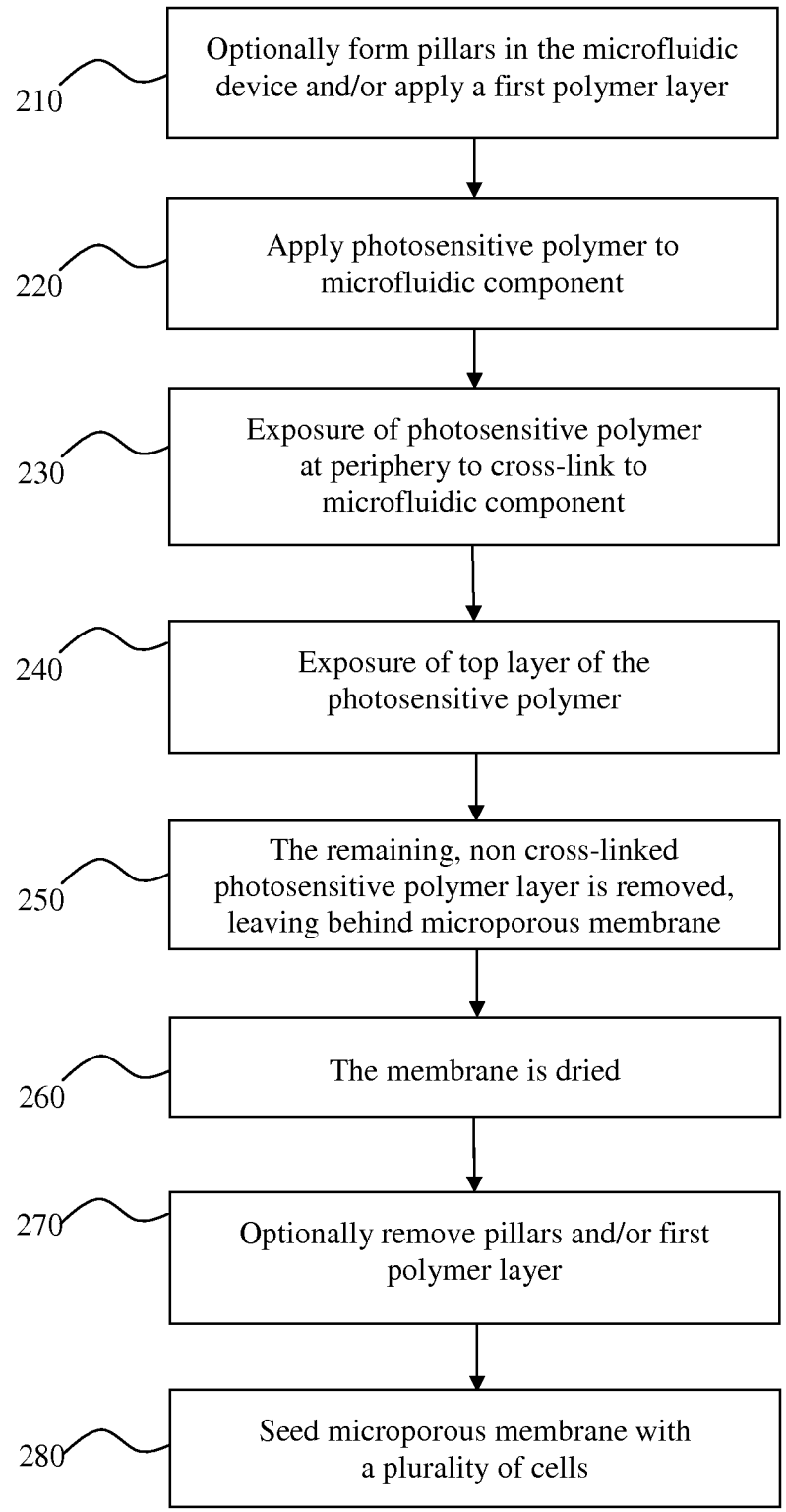
Figure 12:
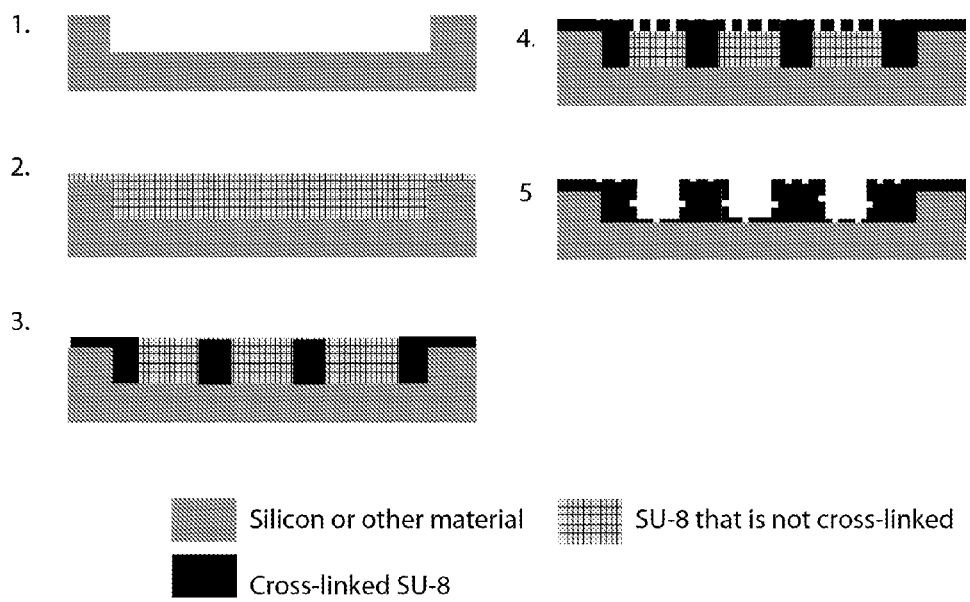
Figure 13:
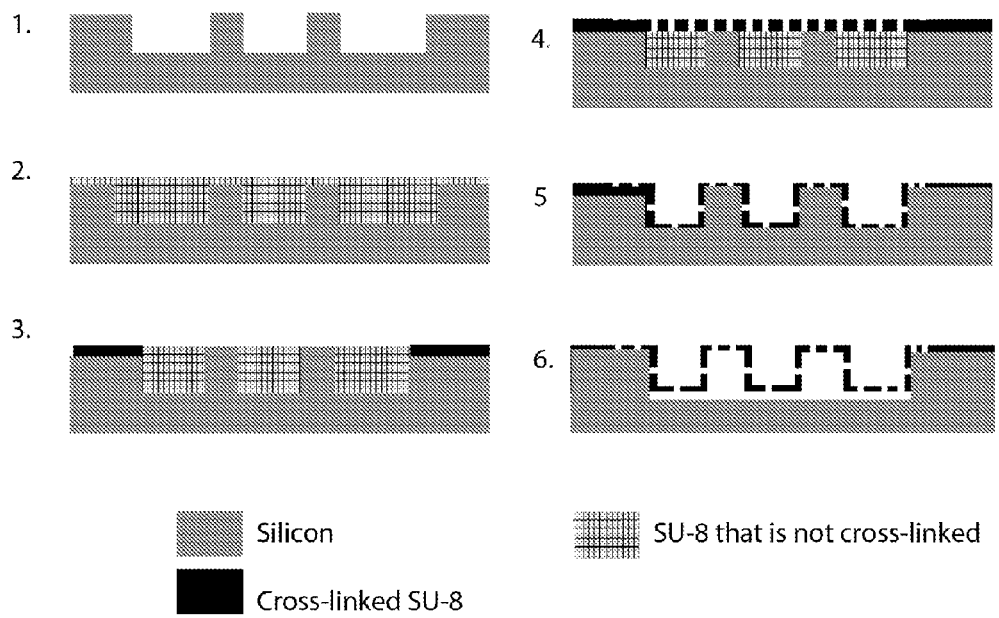
Figure 18:
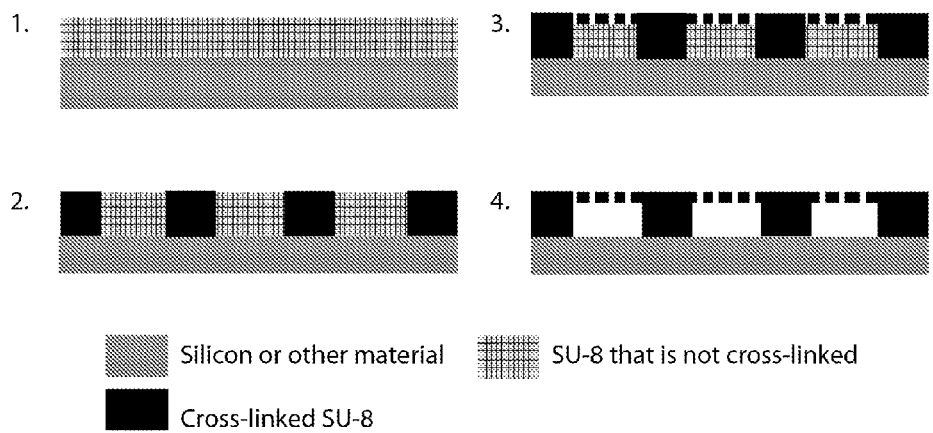
Figure 19:
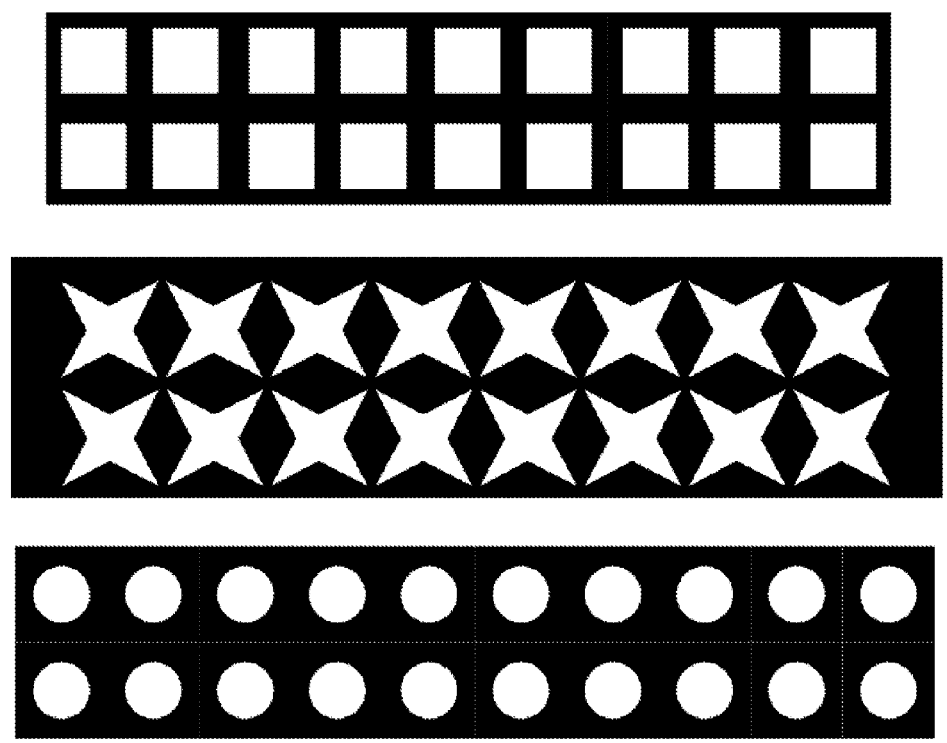

FIG. 4 is a series of confocal microscopy images of three-dimensional cell culture of gastrointestinal epithelial cells (Caco-2) grown for 8 days (A, B, C) and 21 days (D, E, F) on porous membranes dried on silicon pillars (50 µm wide and 200 µm high), according to an embodiment;

FIG. 5 is a series of composite images of Caco-2 cell cultures on 3-D SU-8 membranes draped over silicon pillars according to an embodiment, where A represents 25×25×80 µm pillars with 200 µm distance, B represents 50×50×80 micrometer pillars with 100 µm distance, C represents 100×100×100 µm pillars with 100 µm distance, and D represents 100×100×100 µm pillar with 200 µm distance;

FIG. 6 is a scanning electron microscopy image of a porous membrane shaped over KOH-etched silicon pillars according to an embodiment;

FIGS. 7A-7D are velocity (arrow) and concentration (color) profiles after 50 seconds in a microfluidic device with a porous membrane according to an embodiment, where A is a flat membrane, B is a membrane with aspect ratio of 1, C is a membrane with aspect ratio of 2, and D is a membrane with aspect ratio of 3;

FIG. 8 is a concentration profile graph across the top and bottom layers according to an embodiment;

FIGS. 9A and B are fluid velocity profiles in top and bottom layers according to an embodiment, where A is co-current (flows in the same direction) and B is counter-current (flows in opposite directions);

FIG. 10 is a flowchart of a process for fabricating a microporous membrane according to an embodiment;

FIG. 11 is a flowchart of a process for fabricating a microporous membrane according to an embodiment FIGS. 12-18 are diagrammatic representations of fabrication processes for microfluidic chambers and membranes according to embodiments; and FIG. 19 is a diagrammatic representation of possible masks according to an embodiment.

DETAILED DESCRIPTION OF THE INVENTION

According to an embodiment are microporous, polymeric membranes that contain controllable 3-dimensional shapes that, when populated with cells, mimic key aspects of the intestinal epithelium such as intestinal villi and tight junctions. According to an embodiment, the porous membrane can be flat or contain, for example, 3-dimensional villi with aspect ratios of up to 4:1 or more.

According to one embodiment, the fabrication method uses a photoresist layer (such as a positive resist or a negative resist), such as SU-8, for the fabrication of a microfluidic chamber and a porous membrane that spans across the chamber. Complete cross-linking can be used to form the chamber and a subsequent cross-linking of the SU-8 top layer to form the membrane. Subsequent removal of SU-8 that was not cross-linked and drying yields a flat, porous membrane. The photoresist—also called a "photo-sensitive polymer" or "photo-crosslinkable polymer"—comprises anything where light cross-links the material and the remaining, non-cross-linked material is removed, or where material that was exposed to light is removed and the rest stays behind.

When the chamber and membrane are fabricated on a substrate that contains silicon topography (silicon pillars), the membrane can be collapsed onto that topography so that it takes on the three-dimensional topography. Therefore three-dimensionally structured porous membranes with controlled 3-D shapes are fabricated. The pillars (such as those made of silicon) can be removed (via xenon difluoride etching or any other isotropic etchant), leaving the three-dimensionally shaped porous membrane that is accessible from both sides. The membranes retain their three-dimensional character even after wetting with water, which is important to enable subsequent cell culture. According to another embodiment, the developed membranes can be, among other things, integrated with microfluidic, multi-organ cell culture systems, thereby providing access to both sides, apical and basolateral, of the 3D epithelial cell culture. The developed 2-D and 3D models can be integrated with microfluidic devices that contain tissue compartments for multiple organs. For example, the membrane can be integrated with on-chip multi-organ tissue culture devices that require the presence of the intestinal barrier tissue in addition to other tissues, such as models of the first pass metabolism.

According to an embodiment is a method of fabricating flat or three-dimensionally structured porous membranes that span microfluidic chambers. According to an embodiment, it is possible to control the 3-D shape of the membranes by fabricating pillars of different sizes on the silicon substrate using, for example, deep reactive ion etching or KOH etching and letting the membrane drape over them during drying on air or with nitrogen. According to another embodiment, the sacrificial silicon pillars can be removed via xenon difluoride etching. The silicon etching creates fluidic access underneath the membranes which retain their three-dimensional character even after wetting with water.

According to an embodiment, a porous membrane created pursuant to one of the methods described herein can be fabricated as a microfluidic device is being fabricated, and thus can be directly integrated into the microfluidic culture systems device. Alternatively, the membrane can be fabricated separately from the microfluidic device and incorporated later, or utilized without a microfluidic device. Fabricating the membrane directly at the same time as the device is made enables a leak-free membrane, which is essential for certain uses and research. Existing membranes are sandwiched between two chambers and thus are not able to produce a reliable seal, frequently resulting in leaking.

According to another embodiment is a method of culturing, such as Caco-2 or similar cells for example, on flat or three-dimensionally shaped membranes (without removal of the underlying silicon structure). The growth and the expression of the cells can be characterized for example by occludin, a protein that indicates that tight junctions have been established between cells. Because drug absorption can be predicted with Caco-2 cell monolayers, this cell line has been widely used for in vitro drug absorption assays. Under appropriate conditions, Caco-2 cells form tight junctions and macro villi (between several micrometers and several millimeters tall) similar to the enterocytes lining the normal gastrointestinal (GI) tract epithelium. As a way to improve the current in vitro model, the method is a Caco-2 cell model that mimics the 3-D geometry of intestinal villi. According to this embodiment, the Caco-2 cells are viable and form a 3-D cellular structure conforming to the underlying geometry of the SU-8 membrane. The developed 2-D and 3-D models can be, for example, integrated with microfluidic devices that contain tissue compartments for multiple organs. According to an embodiment, since the membranes are three-dimensional and permeable, the mass transfer of metabolites can occur in either direction that is needed for drug absorption studies, while preventing the cells from migrating through.

Figure 1:
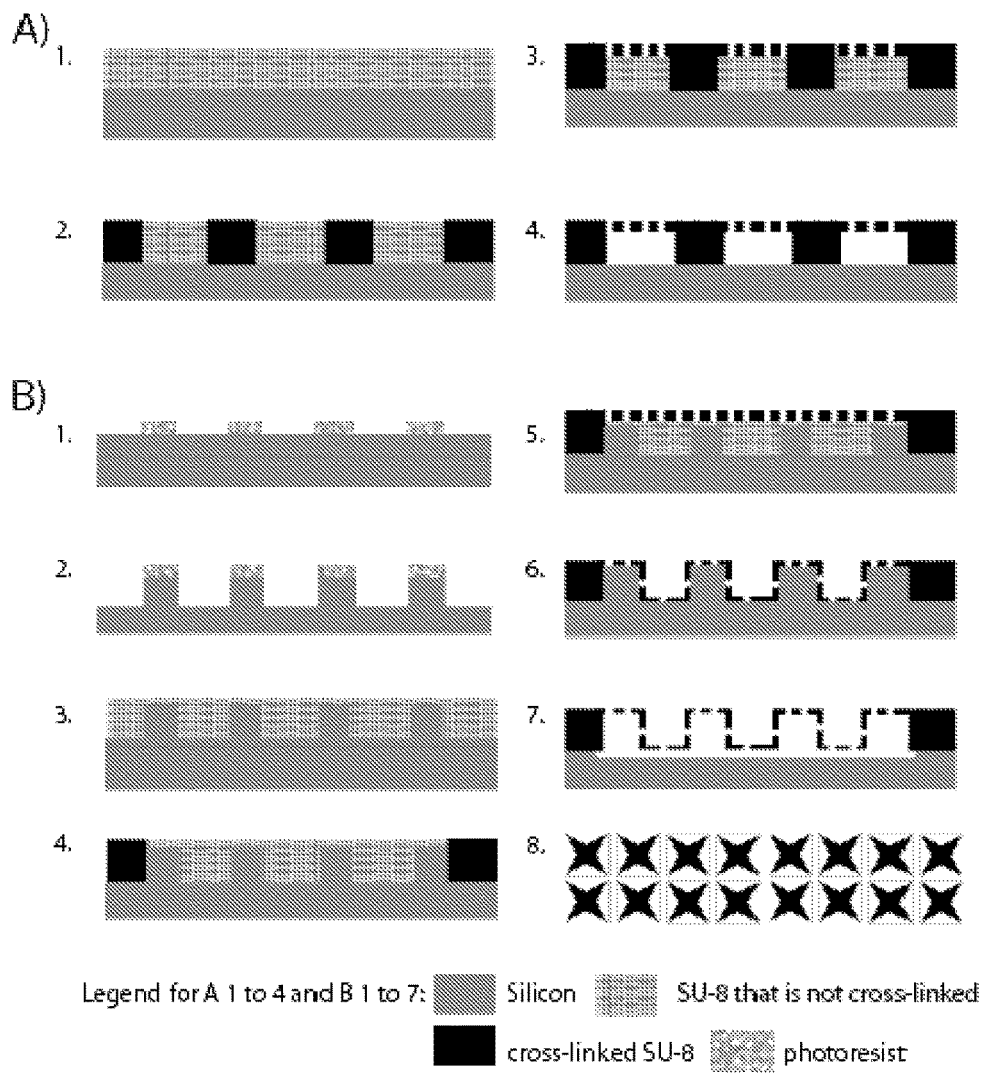
FIG. 1 is a series of diagrammatic representations of a fabrication process for microfluidic chambers and membranes according to an embodiment.

Depicted in FIG. 1 is a schematic representation of embodiments of methods for the fabrication of a 2-D microporous polymeric membrane. In FIG. 1A is depicted an embodiment of a method of membrane fabrication technique consisting of a two-step exposure of a photoresist layer spun on a silicon wafer. This embodiment can be utilized for, among many other things, models of the gastrointestinal tract epithelium. At FIG. 1A 1) is a dual layer created by, for example, spinning of the photoresist and a slowly ramped soft bake (such as SU-8 spinning (2800 rpm for 60 s) and slowly ramped soft bake at 95° C. for 5 min). At FIG. 1A 2) is the exposure of chamber walls and support posts by, for example, a long exposure (such as 720 mJ/cm2). At FIG. 1A 3) is the exposure of membrane with pores with a short and/or partial exposure time that preferably cross-links the top layer only (such as, for example, a 15.6 mJ/cm2 exposure that defines a thinner layer ($\sim$ up to 3 µm, and preferably the top 0.5-4 µm) of the remaining photoresist layer with pores). According to an embodiment, the pores of the membrane can range from as small as 0.1 micrometers up to as large as 1000 micrometers, although other sizes and shapes are possible. At FIG. 1A 4) is the removal with developer of the sacrificial photoresist material remaining (for example, the wafer can be baked (such as 65° C. for 1 min, then 95° C. for 7 min) and developed in photoresist developer for approximately about two hours). As an optional additional step, the wafer can be rinsed with isopropyl alcohol ("IPA") and then dried using a critical point dryer.

In FIG. 1B is depicted an embodiment of a method of 3-D membrane fabrication technique in which porous membranes are formed over pillars with square cross sections of different sizes and densities using photolithography techniques. According to one embodiment, the silicon pillars can comprise square cross sections with sizes such as 25, 50, or 100 µm wide and densities such as 25, 50, 100, or 200 µm between pillars. At FIG. 1B 1) is the patterning of photoresist on a layer such as silicon. At FIG. 1B 2) is the deep reactive ion etching of pillars, such as deep reactive ion etching although other methods of removal/etching are possible. At FIG. 1B 3) is the initial polymer (such as OMNICOAT™ polymer) and photoresist spinning followed by a slowly ramped soft bake. At FIG. 1B 4) is the exposure of microfluidic chamber walls, and at FIG. 1B 5) is the exposure of membrane layer with pores. At FIG. 1B 6) is the removal of sacrificial photoresist with developer and subsequent drying with nitrogen. According to an embodiment, the drying can be done by air, or nitrogen, or any other gas, and it can also be done after the wafer was soaked in water, isopropyl alcohol, or other liquids that evaporate. At FIG. 1B 7) is the removal of OMNICOAT™ polymer to detach the membrane from silicon pillars or removal of silicon pillars with xenon difluoride. At FIG. 1B 8) is an example of pore shapes that can be used in the fabrication of three-dimensionally shaped membranes to ameliorate irregular pore formation due to the diffraction of light.

According to another embodiment is a method of fabricating a two-dimensional microporous polymeric membrane in a microfluidic device. The microfluidic device can be, for example, any such device, including but not limited to lab-on-a-chip or body-on-a-chip systems, among many others. Traditionally, microfluidic devices are created from a substrate in which chambers, channels, and other structures are formed. In most microfluidic devices, fluids are moved, mixed, separated, or otherwise processed, and typically involve either passive fluid control techniques or active transport of fluids by various means (micropumps, micro valves, gravity, centrifugal forces, or other mechanisms known in the art).

There is shown in FIG. 10 a flowchart of a process for fabricating a microporous membrane in accordance with an embodiment. As an initial step 110 of the method, a dual layer is created by, for example, applying a photosensitive polymer to a wafer or a microfluidic device or component. At step 120, the photosensitive polymer is exposed to light to create a plurality of support posts and, at the periphery, chamber walls. This long exposure cross-links the walls of the microfluidic chamber and the structural support posts for the membrane. At step 130, the photosensitive polymer is exposed to light to cross-link the top layer of the photosensitive polymer layer that was not exposed during the first exposure step, preferably using a photolithography mask or similar technique. Examples of mask are provided in FIGS. 1 and 19, although many other variations are possible. The photolithography mask results in the creation of pores within the membrane, thereby creating a porous membrane that is attached to the microfluidic chamber walls. At step 140, the remaining, non cross-linked photosensitive polymer layer underneath the porous membrane is removed. At step 150, the membrane is seeded or cultured with a plurality of cells. Depicted in FIG. 17, for example, is a process for fabricating a two-dimensional microporous membrane on or in an existing microfluidic chamber.

According to another embodiment, the photosensitive polymer itself forms the microfluidic chamber, an embodiment of which is depicted in FIG. 18. According to this embodiment, a layer of photosensitive polymer is applied to a surface, such as a wafer or other surface, or a surface or portion of a microfluidic device. The photosensitive polymer layer is exposed at, for example, the outer portion, or periphery, thereby forming walls that result in the formation of a microfluidic chamber. Together with the previous step or as an additional step, the photosensitive polymer layer can optionally be exposed to create one or more support posts. The remainder of the fabrication method is similar to any of the fabrication methods described or suggested herein. Per this embodiment, a substantially seamless connection is formed between the microfluidic chamber and the membrane because both are formed from the same initial photosensitive polymer layer.

There is shown in FIG. 11 yet another embodiment of a method of fabricating a microporous polymeric membrane in a microfluidic device. Again, the microfluidic device can be, for example, any such device, including but not limited to lab-on-a-chip or body-on-a-chip systems, among many others. Depicted in FIGS. 12 and 13 for example, are embodiments wherein a three-dimensional microporous membrane is fabricated in or on an existing microfluidic chamber.

At optional step 210 of the method depicted in FIG. 11, pillars are formed in the microfluidic device through any means known in the art, including but not limited to deep reactive ion etching or KOH etching. According to another embodiment, the pillars are already formed in the microfluidic device or chamber prior to applying the photosensitive material layer. Alternatively, the pillars are formed by exposure of the photosensitive material, or are formed of silicon or other material. As yet another embodiment, no pillars are found or formed under the layer of photosensitive material. If pillars are utilized they can be, for example, any one of a wide variety of shapes and sizes, including rounded, slanted, pointed or with sharp edges, straight, short and wide, tall and thin, or any other shape or size. According to some embodiments, the shape and/or size of the pillar is selected based on the use of the membrane, including, for example, the tissue type to be mimicked.

Also at optional step 210 of the method depicted in FIG. 11, or at a following step, a first polymer layer can be deposited or applied to the microfluidic device. The first polymer layer can be, for example, a primer for photoresist coating. Suitable primers including OMNICOAT™ polymer (an organic polymer solution comprising mostly cyclopentanone and propylene glycol monomethyl ether, among other proprietary components), or any other polymer or compound which can be sacrificed or removed as needed.

At step 220, a photosensitive polymer layer is applied. If a first polymer layer has been utilized, then the photosensitive polymer is applied over the first polymer layer. At step 230, the photosensitive polymer is exposed to light to cross-link the membrane's periphery to the walls of the microfluidic chamber. At step 240, the photosensitive polymer layer is exposed to light to cross-link the top layer of the photosensitive polymer layer that was not exposed during the first exposure step, preferably using a photolithography mask or similar technique. The photolithography mask results in the creation of pores within the membrane, thereby creating a porous membrane that is attached to the microfluidic chamber walls. At step 250, the non-cross-linked photosensitive polymer layer is removed. At step 260, the membrane is dried. Drying allows the membrane to adopt the three-dimensional shape it is in as it dries, including protrusions caused by resting on the pillars, even if the pillars are later removed.

If pillars and a first polymer layer have been utilized in the process, at step 270 the first polymer layer can be removed in order to detach the membrane from the pillars. Alternatively or additionally, the pillars can be removed in order to create the space underlying the membrane, including by methods such as by xenon difluoride among other mechanisms.

At step 280, the membrane can be seeded or cultured with a plurality of cells.

Figure 14:
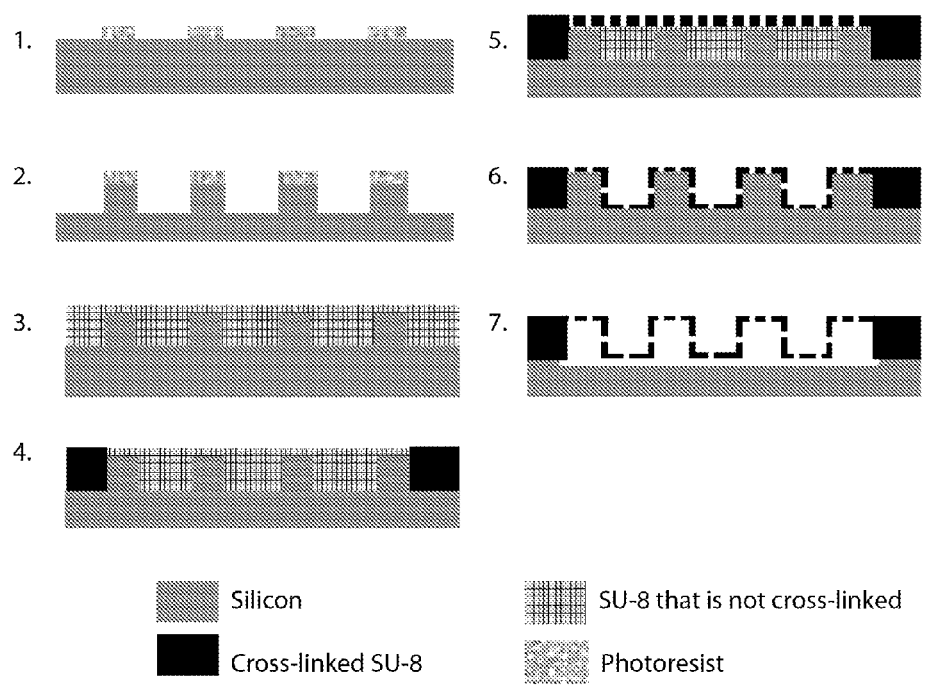
Figure 15:
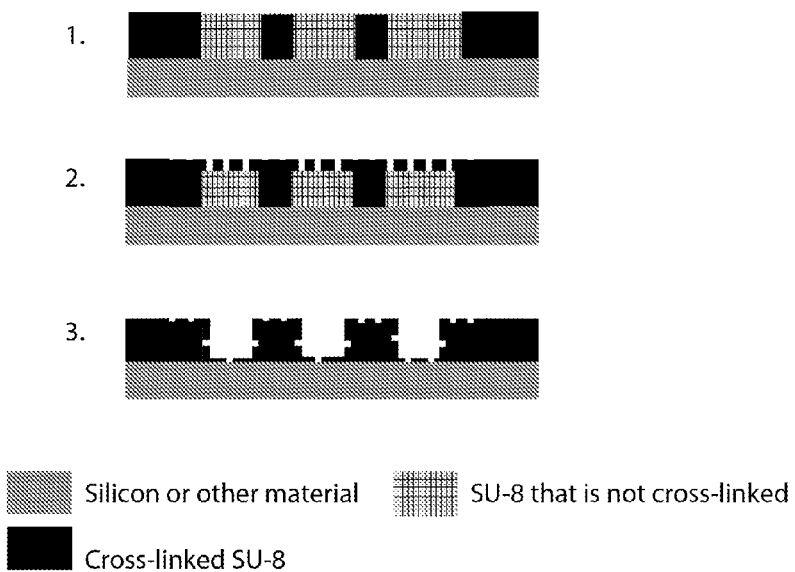
Figure 16:
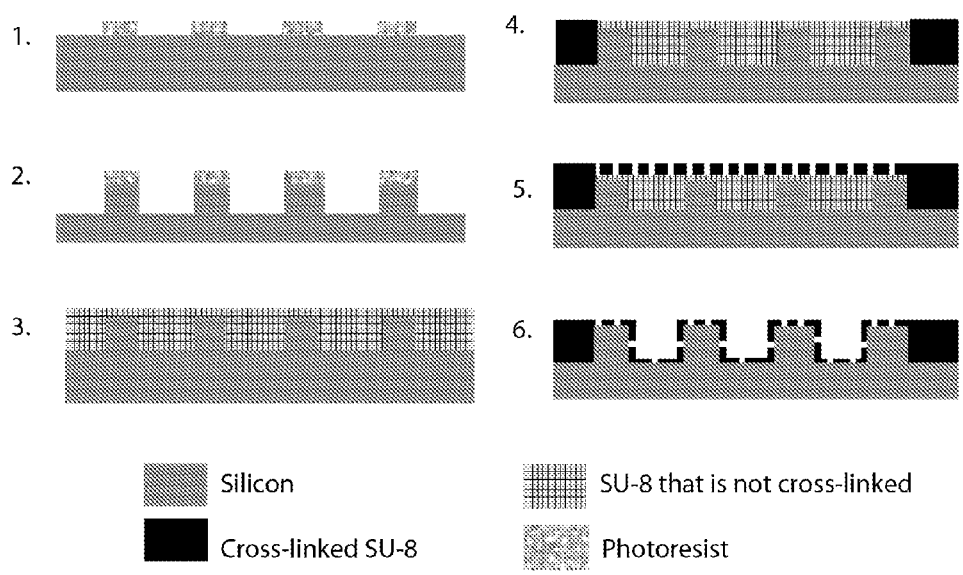
Figure 17:
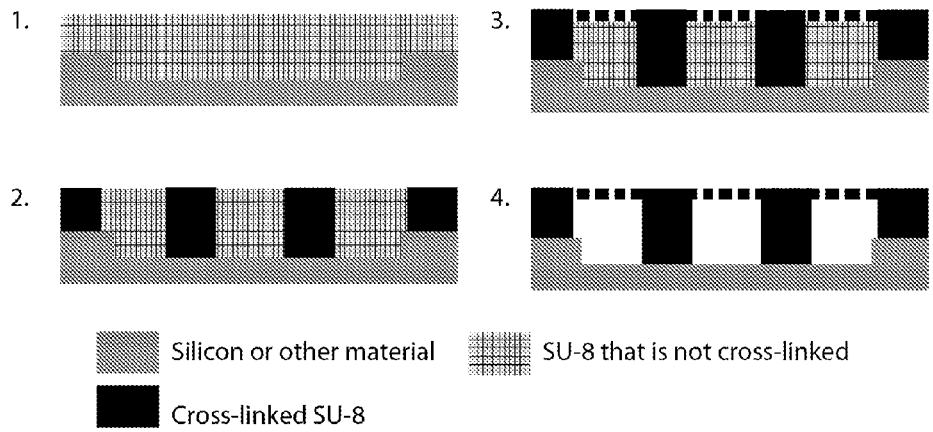

According to another embodiment, the photosensitive polymer itself forms the microfluidic chamber surrounding or around the three-dimensional membrane. Examples of this embodiment are depicted in FIGS. 14-16. According to this embodiment, a layer of photosensitive polymer is applied to a surface, such as a wafer or other surface, or a surface or portion of a microfluidic device. The photosensitive polymer layer is exposed at, for example, the outer portion, or periphery, thereby forming walls that result in the formation of a microfluidic chamber. Together with the previous step or as an additional step, the photosensitive polymer layer can optionally be exposed to create one or more support posts. Alternatively, pillars can exist on the surface previously, or there can be no pillars or support posts. As yet another embodiment, a first polymer layer can be applied before the photosensitive polymer layer is applied. The remainder of the fabrication method is similar to any of the fabrication methods described or suggested herein. Per this embodiment, a substantially seamless connection is formed between the microfluidic chamber and the membrane because both are formed from the same initial photosensitive polymer layer.

According to yet another embodiment, a two-dimensional or three-dimensional porous membrane can be fabricated according to one of the methods described or suggested herein and then transferred to a non-microfluidic membrane support. The transfer can be done, for example, using a support material such as paraffin, as the membrane itself might be too weak to be transferred without a support. As membrane materials develop, a support may not be necessary.

As just one example of a method for fabricating a membrane and then transferring that membrane to a non-microfluidic membrane support, a photosensitive layer is first applied to a surface, wafer, microfluidic device, or microfluidic chamber. The photosensitive layer can then be exposed to light to cross-link the top layer of the photosensitive polymer layer, preferably using a photolithography mask or similar technique. Any of the methods described or suggested herein can be used to create a membrane with a two-dimensional or three-dimensional shape. The remaining, non cross-linked photosensitive polymer layer underneath the porous membrane can then be removed, leaving behind a microporous membrane. At a next step, the membrane is removed from the fabrication surface and is added, appended, glued, cross-linked, or otherwise utilized in another chamber, device, or apparatus.

Example 1—Fabrication of Microfluidic Chambers with Flat Porous Membranes

According to one embodiment, a membrane fabrication technique consists of a two-step exposure of a 50 µm thick SU-8 layer spun on a silicon wafer. The first exposure defines the walls of the microfluidic chamber as well as membrane support posts inside the chamber. The second exposure is a partial exposure that cross-links the top 0.5-4 µm of the remaining SU-8. An embodiment is represented in FIG. 1A.

Other photosensitive materials may be used, including but not limited to KMPR, acrylate-based Intervia BPN, and many other materials.

According to one aspect, a 50 µm thick layer of SU-8 2050 (Microchem, Newton, Mass.) was spun-coated onto a silicon wafer at 2800 rpm for 60 sec and soft baked at 65° C. for 2 min, then 95° C. for 5 min before patterning using the EV620. Patterning of the SU-8 via the contact aligner was separated into two exposure steps: a long exposure (720 mJ/cm$^2$) that defines the microfluidic chamber and supporting SU-8 posts, and a short exposure (15.6 mJ/cm$^2$) that defines a thinner layer (~ up to 3 um) of SU-8 with pores. After exposing both layers, the wafer was baked (65° C. for 1 min, then 95° C. for 7 min) and developed in SU-8 developer for at least two hours. The wafer was then rinsed with isopropyl alcohol (IPA) dried using a critical point dryer.

Example 2—Fabrication of Microfluidic Chambers with Porous Membranes for Three-Dimensional Caco-2 Cell Culture According to one embodiment, porous membranes were formed over silicon pillars with square cross sections of different sizes (25, 50, or 100 µm wide) and densities (25, 50, 100, or 200 µm between pillars) using conventional photolithography techniques. An embodiment is represented in FIG. 1B. Briefly, silicon wafers were primed with P-20 primer (Shin EtsuMicroSi, Tokyo, Japan) at 3000 rpm for 30 sec and then spin coated with a 2-μm-thick layer of SC™ 1827 photoresist (3000 rpm for 30 sec) (Shipley, Marlborough, Mass.) baked for 1 min at 115° C. Pillar arrays were then patterned into the photoresist at 96 mJ/cm$^2$ with an EV620 contact aligner (Electronic Visions Inc., Phoenix, Ariz.) and developed in AZ 300 MIF (AZ Electronic Materials, Somerville, N.J.) for 1-2 min. Pillars 100 um tall were etched into the silicon via Bosch fluorine etch (Unaxis 770 Si Etcher, Plasma-Therm Inc., St. Petersburg, Fla.) and the remaining SC™ 1827 was stripped via oxygen plasma (GaSonics Aura 1000 Asher).

After dehydrating the wafer at 170° C. for 15-20 min to improve adhesion, a sacrificial layer (OMNICOAT™ polymer) was spun onto the wafer. Then a 110-um-thick layer of SU-8 2050 (Microchem, Newton, Mass.) was spin coated onto the wafer at 1700 rpm for 60 sec and soft baked at 65° C. for 5 min, then 95° C. for 20 min before patterning using the EV620. Patterning of the SU-8 via the contact aligner was conducted with two exposure steps: a long exposure (720 mJ/cm$^2$) that defines the microfluidic chamber around the pillar array, and a short exposure (15.6 mJ/cm$^2$) that cross-links the top layer (0.5-2.5 um) of SU-8 with the exception of pores. After conducting both exposures immediately following each, the wafer was baked (65° C. for 5 min, then 95° C. for 10 min) and developed in SU-8 developer for at least two hours, then rinsed with isopropyl alcohol (IPA). The wafers were then left to dry on air under a lamp for at least 30 min. The OMNICOAT™ polymer (Microchem, Newton, Mass.) release layer was removed with developer so that the membrane was detached from the silicon pillars, creating space for fluidic flow. Images of membranes were obtained with an optical microscope (Fisher Scientific, Hampton, N.H.) and microscope camera (Nikon); cross sections were obtained by cleaving and imaging with a Zeiss Ultra 55 scanning electron microscope (Carl Zeiss, Thornwood, N.Y.).

Example 3—Fabrication of Microfluidic Chambers with Three-Dimensional Porous Membranes and Increased Chamber Depth According to another embodiment, silicon pillars were created using an alternative method. Pursuant to this method a silicon nitride film was grown (500 nm) at 1100° C. on silicon wafers (Silicon Quest, Santa Clara, Calif.) using the process gases $SiH_2Cl_2$, $NH_3$, and $N_2O$ in a furnace tube. The wafers were then coated with photoresist S1813 (Shipley, Marlborough, Mass.) at a spin speed of 3000 rpm and the area surrounding the pillars was exposed for 4 s using an AB-M HTG 3HR contact aligner (AB-M, San Jose, Calif.). They were then developed for 2 min and the exposed silicon nitride was removed using a reactive ion etcher (Oxford 80, Oxford Instruments, Tubney Woods, Abingdon, Oxfordshire, OX13 5QX, UK) with 50 sccm CHF3 and 2 sccm O2 at 50 mTorr and 200 W. The exposed substrate was etched to a depth of 20 μm using a 50% KOH solution at 80° C. The remaining silicon nitride was removed with a reactive ion etcher (Oxford 80, Oxford Instruments, Tubney Woods, Abingdon, Oxfordshire, OX13 5QX, UK) with 50 sccm CHF3 and 2 sccm O2 at 50 mTorr and 200 W. SU-8 was then spun and exposed as described above. After air-drying the SU-8 membrane, the wafer was exposed to xenon-difluoride using a Xactix xenon difluoride etcher (XACTIX, Inc., Pittsburgh, Pa. 15203 USA). Forty cycles with 20 s per cycle at 4 Torr xenon difluoride gas pressure was used. The samples were then cleaved to expose their cross-section, which was imaged with a Zeiss Ultra 55 scanning electron microscope (Carl Zeiss, Thornwood, N.Y.).

Example 4—Cell Culture and Chemicals

Caco-2 cells (ATCC HTB 37, Manassas, Va.) were thawed at passage 28 and used for experiments at passage 41-60. Cells were maintained in Dulbecco's modified Eagle medium with 4 mM GlutaMAX and 4.5 g/L D-glucose (DMEM, Invitrogen, Grand Island, N.Y.) supplemented with 20% heat inactivated fetal bovine serum (HI FBS, Invitrogen) every 2-3 days. Rabbit anti-occludin monoclonal antibody, secondary antibodies (Alexa 555- or Alexa 568-conjugated goat anti-rabbit IgG), and normal goat serum were obtained from Invitrogen. The blocking solution for immunostaining wash steps, 1% DPBSA, was made from 1% (w/v) bovine serum albumin (BSA) (Sigma Aldrich, St. Louis, Mo.) dissolved in DPBS (Invitrogen).

Example 5—Caco-2 Cell Culture on Membranes and Characterization of the Cell Layer Membrane samples were sterilized by soaking them in IPA for at least 15 min. They were then washed three times with PBS and coated with 4 ug/cm$^2$ of poly-D-lysine (Sigma Aldrich) for 5 min, washed with an equal volume of DPBS, coated with 8 ug/cm$^2$ of Type I collagen (BD Biosciences, Bedford, Mass.) for 1 h and washed again with DPBS to promote cell attachment and migration. Caco-2 cells were then seeded on samples at a density of 281,000 cells/cm$^2$, which covered the base of the villi after 24 h. Cell proliferation was monitored by staining the cells with CellTracker (Molecular Probes) 24 h after seeding. Each sample was re-stained every 4-5 days thereafter. After 8, 15, 18, and 22 days of cell culture (separate samples), the samples were fixed in formaldehyde, washed 3 times for 5 min in 1% DPBSA, and then permeabilized with Triton X-100 in 2.5% DPBSA for 5 min. The samples were washed 3 times again, incubated with rabbit anti-occludin antibody (or 5% normal goat serum in blocking solution for negative control) for 45-55 min, and incubated with goat anti-rabbit antibody tagged with either Alexa Fluor 555 (only samples that were stained on day 8) or Alexa Fluor 568 for 45-5 5 min with 3 times 5 min washes after each step. After occludin staining, the samples were incubated simultaneously with Alexa Fluor 488 phalloidin (Invitrogen) and TO-PRO-3 (Invitrogen) to stain for filamentous actin (F-actin) and nuclear DNA, respectively. Samples were then scanned with a Leica SP2 confocal microscope (Leica Microsystems, Bannockburn, Ill.) and 3-D images were rendered using Volocity (PerkinElmer, Waltham, Mass.).

Example 6—Simulation of Flow in Microfluidic Chambers with Three-Dimensionally Structured Membranes The fluid velocity and diffusion profiles inside a microfluidic device integrated with SU-8 membranes were simulated using Comsol multiphysics (Burlington, Mass., USA). The geometries of the flat and 3-D SU-8 membranes were drawn in 2-D, and the incompressible Navier-Stokes and convection-diffusion multiphysics were used. The parameters used in the simulation are summarized in TABLE 1, although other parameters and variations are possible.

TABLE 1

Simulation Parameters

| Parameter | Value | Unit |
|---|---|---|
| Density | 1000 | kg/m$^3$ |
| Viscosity | $1 \times 10^{-3}$ | Pa s |
| Inflow velocity | $7.5 \times 10^{-5}$ | m/s |
| Diffusion coefficient | $3 \times 10^{-10}$ | m$^2$/s |
| Incoming fluid concentration in top chamber | 1 | mM |

Example 7—Fabrication of Microfluidic Chambers that Contain Flat, Porous Membranes Using an embodiment of a method described herein, microfluidic chambers were fabricated (8 mm wide, 10 long, 50 μm deep) that were covered by flat, SU-8 membranes. The membranes were 0.5-2.5 μm thick with pore sizes that ranged from 0.5-4 μm. Both microfluidic chambers and porous membranes were fabricated in a one fabrication sequence that can be completed in one day. The principle fabrication protocol relies on a two-step exposure. The first exposure crosslinks the walls of the microfluidic chamber as well as the structural support posts for the membrane (for this set of experiments, the supporting posts were 50×50 μm wide and 75 μm apart from each other). The second exposure crosslinks the top layer of the resist that was not exposed during the first exposure step. This is achieved by using a very short exposure time (typically between 10 s to 20 mJ/cm$^2$, 365 nm light) that is not sufficient to cross-link the entire SU-8 layer. Cross-linking the top layer creates a thin SU-8 membrane that is attached to the microfluidic chamber walls that were cross-linked in the first exposure step. Using a photolithography mask that contains pores for the short exposure step creates pores within the membrane. The pores allow for the subsequent removal of the unexposed SU-8 underneath the membrane. Partial SU-8 exposure has been previously used to fabricate microelectromechanical systems (MEMS) and structures that have been used as molds for complex microfluidic PDMS devices. Utilizing the high contrast capability of SU-8 and partial exposure of the material, microfluidic chambers that are covered by a porous membrane are created.

According to this embodiment, the thickness of the fabricated membranes ranged from 0.5 μm at their thinnest region to 2.5 μm and is well suited to enable mass transport with low resistance. The membranes are thicker than those that can be fabricated with silicon nitride (200 nm-1 μm), but thinner than commercially available membranes. The energy used to cross-link the membrane determines its thickness because it decays with distance from the top and reaches a level that becomes insufficient to cross-link material that is farther away from the light source. Exposure energies used to create membranes ranged from 10 to 20 mJ/cm$^2$. Membranes that were underexposed and overexposed were subject to cracking during drying. Membranes that were at least 0.5 μm thick at their thinnest areas were robust enough to withstand the process of drying without cracking, see FIG. 2.

The described fabrication process can thereby create membranes with pore sizes ranging from, for example, 0.5-4 μm. Since SU-8 layers are not perfectly flat and diffraction of light occurs during contact photolithography, the exposure energy used to crosslink the membranes also influences the pore size. However, since the range of exposure energies that cross-link the SU-8 that later constitutes the membrane is small, the pore size is not affected beyond control and can be adjusted by increasing or decreasing the pore size in the array of pores in the mask. For example, masks that contained an array of 3×3 μm pores were exposed with 20 mJ/cm$^2$ resulted in rounded pores that were 2.5 μm in diameter. The magnitude of decrease in size depends on each sample since the flatness (or lack of flatness) of a sample contributes to the decrease. To create membranes with a desired thickness and pore size, the energy that is necessary to result in a particular thickness of the membrane can be determined first and then the pore size can be adjusted by adjusting the sizes of pores on the mask. Despite the rounding of the pores and variability in sample flatness, the pore sizes achieved were relatively uniform throughout the membrane, see FIG. 2.

According to an embodiment, the support posts that serve as structural support can be, for example, 50×50 μm in size, although many other sizes and shapes are possible. They can be spaced 75 μm apart from one another, although other densities are possible.

According to an embodiment, in the places at which the support posts support the membrane, the membrane is not porous. Hence in an example the support posts decrease the area of the membrane that contains pores by 32%. The porosity of the porous area alone depends on the pore size and was estimated to be between 9.7%-56.7%. The porosity of the entire membrane area, including the post area was between 4.4%-25.3%. The maximum porosity achieved is higher than that of commercially available membranes (~10% porosity at a membrane thickness of 10 μm). It is possible to increase the porosity of the presented membranes by decreasing the percentage of the area without pores by decreasing the size of the support posts and spacing them farther apart. When spacing them farther apart it may be necessary to dry the devices via critical point drying, so that the membranes do not collapse onto the substrate during air-drying. Higher porosity is desired to place the primary resistance for mass transfer on the cell layer rather than the membrane.

Figure 2:
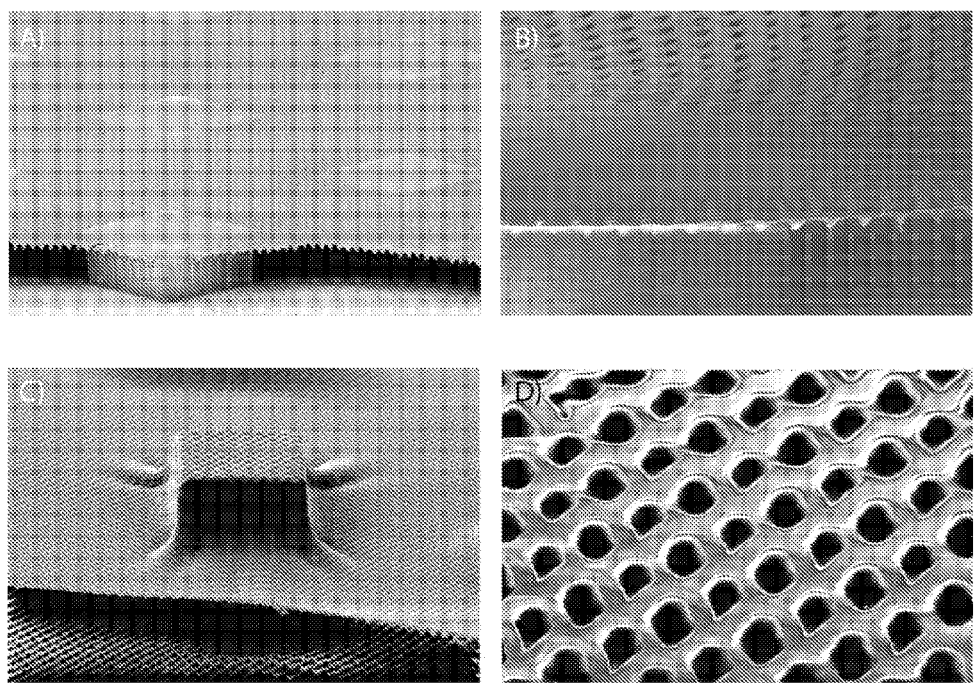
FIG. 2 is a series of images of porous membranes anchored to and spanning across microfluidic chambers, according to an embodiment.
Figure 3:
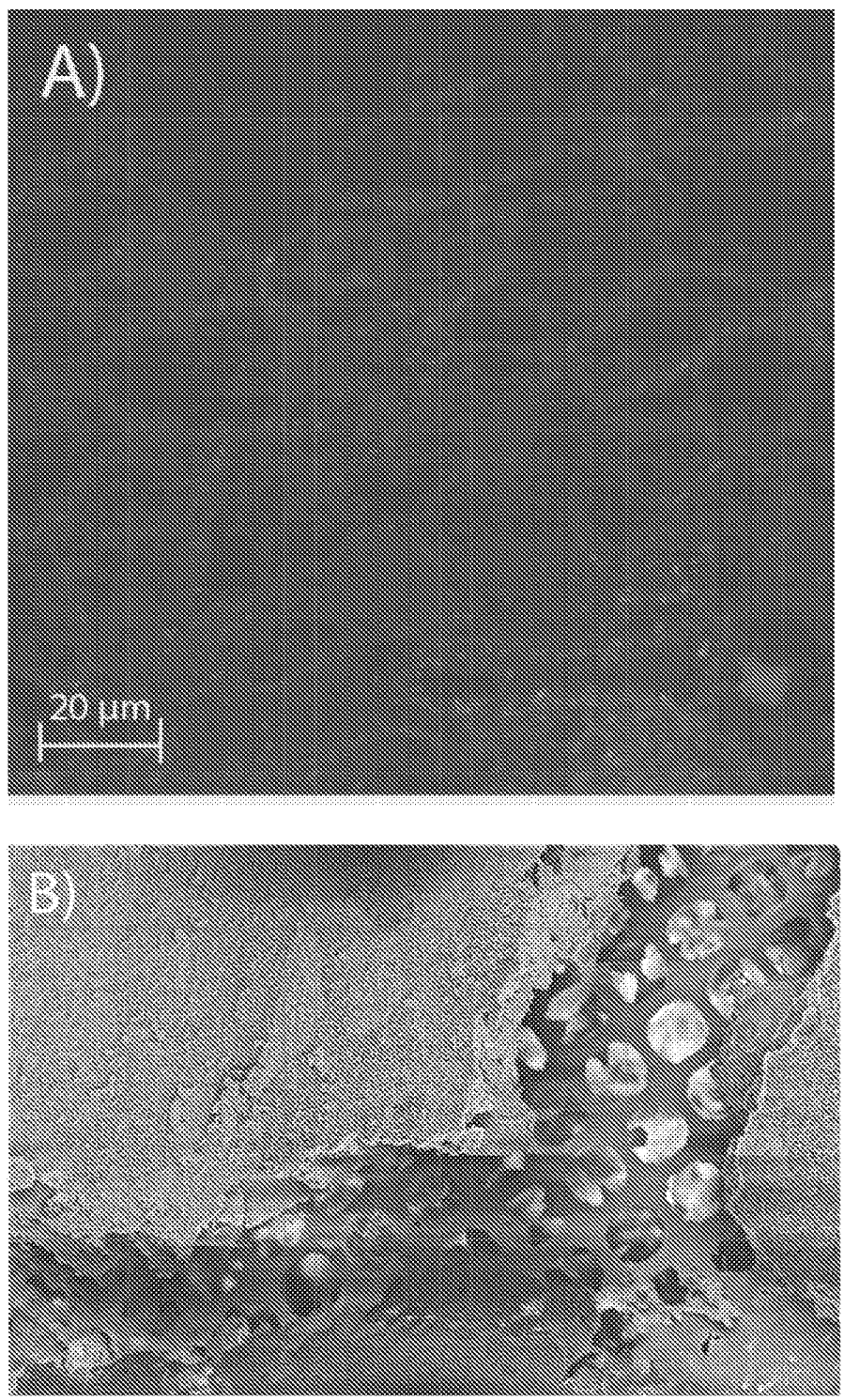
FIG. 3 is a series of images of Caco-2 cell growth on porous membranes according to an embodiment, where

Example 8—Fabrication of Microfluidic Chambers with Membranes that are Shaped in the Form of Small Villi Structures Drying the membranes over support posts that are spaced at least 150 μm from one another produces membranes that drape over the posts, forming curved membrane surfaces hanging over the posts, as shown for example in FIG. 2. The curvature and the height of the membranes are determined by, for example, the height, size and the distance between of the posts. When the posts consist of silicon instead of SU-8, i.e. if the SU-8 membrane fabrication is preceded by a step that creates silicon pillars via deep reactive ion etching or KOH etching, a small space can be created between the membrane and the silicon. For this purpose a sacrificial layer (such as OMNICOAT™ polymer) was spun onto the silicon before SU-8 spinning. This layer can be removed after the membranes have formed. The membrane is this separated from the underlying surface and can allow small amounts of liquid to access the underside of the membrane.

According to an embodiment, the width of pillars tested was 25, 50, and 100 μm, the distance between the pillars was 25, 50, 100, and 200 μm, and the height of the pillars was between 40 and 100 μm. The fabricated pillar structures had aspect ratios ranging from 1:0.5 to 1:4. The spacing between the pillars needed to be at least twice the width of the pillars to ensure that the SU-8 membranes reached the substrate between the pillars. One goal was to re-create in vivo sizes of gastrointestinal villi, which are 500 µm high. Increasing the height of pillar structures is traditionally challenging, as higher pillars require a larger surface area of photoresist to hang over the pillars and the material is more prone to tearing during drying. It is also necessary to create SU-8 membranes that are thinner to render it more flexible. Thinner SU-8 membranes were used for the highest aspect ratio pillars worked with. They were obtained by decreasing the exposure energy from 20 mJ/cm$^2$ to 15.6 mJ/cm$^2$.

Since SU-8 spinning over high aspect ratio silicon pillars creates relatively uneven SU-8 layers compared to SU-8 that was spun on a flat surface, the pore sizes of the pores that are created during the exposure with a contact photolithography tool were not as uniformly distributed as on the flat membranes described above. To decrease the effect of light diffraction on the pore geometry, the pore geometry on the lithography mask was adjusted. The diagram in FIG. 1B shows a suitable pore geometry for the mask. This geometry prevents additive cross-linking in the spaces between pores.

Example 9—Two-Dimensional and Three-Dimensional Caco-2 Cell Models of the Intestinal Epithelium According to an embodiment, in order to create two dimensional and three-dimensional microfluidic models of the intestinal epithelium the surfaces of the fabricated membranes were modified with poly-D-lysine and collagen and seeded Caco-2 cells on them. On both, flat membranes and three-dimensional membranes, the Caco-2 cells grew with normal morphology and reached 100% coverage within 21 days of seeding. This observation is comparable to Caco-2 cell growth observed on commercially available membranes that were modified with collagen prior to cell seeding. The membranes were mechanically strong enough to support cell growth without breaking, as shown in FIG. 3B. FIG. 3A is an image of Caco-2 cells that were immunostained for actin (green) and occludin (red). Further, Caco-2 cells developed tight junctions on both types of membranes, indicating that the cell density has reached the critical level that is necessary to establish the barrier function of the model. Occludin is a protein that is part of tight junction complexes, which develop between all gastrointestinal epithelial cells when they come in close contact with each other. These junctions limit the transport of substances through the intercellular space. They are a key feature of the in vivo epithelium of the gastrointestinal tract. FIG. 3A is a fluorescence microscopy image of Caco-2 cells grown for 21 days on flat SU-8 membranes. The cells were fixed and immunostained for occludin. Visual inspection revealed that the membrane was fully covered with occludin-expressing Caco-2 cells. On three-dimensional membrane surfaces, cells settled at the membrane valleys first and then spread onto the pillars.

FIGS. 4 and 5 are confocal fluorescence images of the Caco-2 cells cultured on three-dimensional SU-8 membranes. Immunostaining for the nucleus (blue), actin (green), and occludin (red) after 8 days of culture and subsequent fluorescent imaging revealed that Caco-2 cells covered an estimated 80% of the area at this time. The sidewalls of 50 µm high pillars were also covered, but not their top surfaces (see, e.g., FIGS. 4A, B, and C). Occludin expression was visible on many cells, but not visible throughout the entire cell layer, indicating that the cell density was yet too low for establishing the barrier function of the cell layer. After 21 days of cell culture the entire membrane area, including the sidewalls and top surfaces of the pillars was covered with Caco-2 cells (100% according to visual inspection) (see, e.g., FIGS. 4D, E, and F). Tight junctions as shown via occludin immunostaining were well developed throughout the cell layer (see, e.g., FIG. 4E).

When the spacing between the pillars was less than 100 µm, cells often merged into a single cell mass rather than forming separate pillar shapes. This phenomenon was more evident when cells were cultured for longer than 14 days. Within the combinations tested, 50 or 100 µm wide pillars with 100 or 200 µm spacing gave the best coverage. This result is promising since the density of the pillar structures is close to that of human intestinal villi, which is about 25 villi per mm$^2$.

Since Caco-2 cells grew on all fabricated membranes with comparable morphology to that observed on commercially available membranes, it is concluded that the fabricated membranes fulfill the requirements needed to culture epithelial cells on them. The requirements for this are that the membrane can span across microfluidic chambers that are several millimeters wide and long, that it is mechanically stable enough to support cell growth, and that it accommodates mass transport through the cell layer via pores. The pores must be large enough to enable the exchange of metabolites, but small enough to prevent cells from migrating through. At the same time, the membranes must be thin enough to allow for efficient transport of molecules and at the same time thick enough to withstand physical forces originating from cellular attachment and microfluidic flow. The membrane's mechanical stability was sufficient to support the culture of Caco-2 cells that formed tight junctions. The Caco-2 cells cultured on the fabricated membranes are an on chip in vitro model of the epithelium of the gastrointestinal tract that can be integrated with other organ compartments to create multi organ cell culture devices for drug testing.

Example 10—Creating Varying Chamber Depths in Microfluidic Devices with Flat and with Three-Dimensional Porous Membranes According to an embodiment are porous membranes with unique and beneficial characteristics. For example, in order to simulate the digestive system and the systemic circulation, two microfluidic streams that access the apical and basolateral sides of the Caco-2 cell layer separately from one another are typically needed. According to an embodiment, when fabricating flat membranes the basolateral microfluidic chamber is created during the first exposure, immediately followed by a second exposure that creates the membrane. Only one development step is needed to yield a membrane that is attached to the chamber walls. The design is leak-free and the membrane does not need to be handled outside the fluidic device. No gaskets are needed to prevent leakage. Although it is possible to construct the apical chamber with photoresist as well, it can also be micromachined it into a plexiglass top piece that also contained an embedded electrode. This design lends itself to the integration of electrodes that can evaluate the quality of the barrier function of the epithelial cell layer.

Fluidic access to the basolateral chamber of systems with three-dimensionally shaped membranes is limited when the gap between the membrane and the chamber floor is created by dissolving a thin sacrificial layer that was spun on the wafer before SU-8 processing. To obtain better access to the basolateral side of the cells (i.e. the underside of the membrane), the microfluidic chambers were dry etched with xenon difluoride. Xenon difluoride diffused through the membranes pores, accessed the silicon underneath and etched it isotropically. Using xenon difluoride at 4 Torr for 40 etch cycles that lasted 20 s each, the silicon pillars were removed and a larger chamber depth was created, as show for example in FIG. 6. Three-dimensionally shaped membranes retained their shape after etching as well as after immersion in water. The experiments discussed here present the first microfabricated porous membranes that are integral parts of microfluidic systems and that are shaped three-dimensionally.

Membranes with three-dimensional villi structures can be used to investigate hypotheses that aim to explain the difference in predictive value of mass transport across Caco-2 monolayers between fast and slowly absorbed drugs. While the absorption rate of fast absorbing drugs compares well to that seen in vivo (the absorption difference is only 2- to 4-fold) the absorption of slowly absorbed drugs is about 50-fold slower in the in vitro model compared to in vivo. This effect could be related to the smaller surface area that is available in the in vitro model due to the lack of macro villi. It has been theorized that drugs that slowly absorb concentrate at the villous tips, resulting in a concentration gradient that supports the drug's diffusion into the intervillous space. These hypotheses could be tested with microfluidic systems fabricated with the described methods.

Figure 9B:
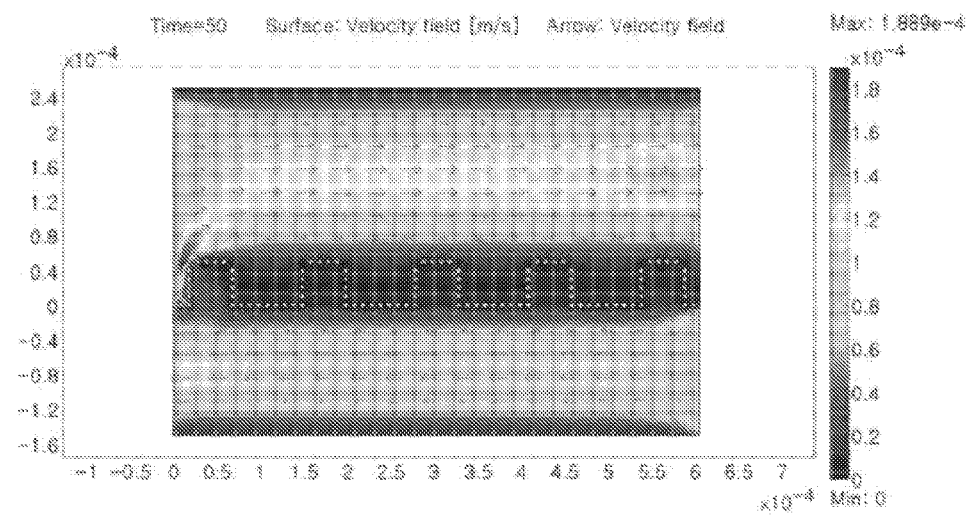

Example 11—Simulation of Convection/Diffusion Profiles Inside Microfluidic Chambers with Three-Dimensionally Shaped Membranes Shown in FIG. 7 are velocity (blue arrows) and concentration (color map) profiles after 50 s. Due to the obstruction of the pillars, the space between the pillars maintain almost stagnant flow pattern. As the height of the pillars increases, the area of stagnant flow becomes greater. Also the simulation result indicates that diffusion occurs quicker with increasing aspect ratio of the pillars. This can be explained by the increase in the permeable surface area with increasing aspect ratio. In addition, increasing the aspect ratio affects the flow velocity in the upper channel, increasing the velocity. A higher flow velocity results in a faster transport across the membrane. Shown in FIG. 8 is a plot of the concentration profiles across the height of the microfluidic device at time 50 s. When the aspect ratio is greater than 2, the concentration profile becomes much flatter. The convective mixing between the top and bottom layer was almost negligible, as the fabricated membrane with 5 μm pore size provides sufficient fluidic resistance. This was true regardless of the direction of the flows in the top and bottom layers, as shown in FIG. 9. Having opposite flow directions in the top and bottom layers did not affect the diffusion profiles across the membranes, regardless of the aspect ratios of the pillars.

According to various embodiments, the 2D and 3D shaped membranes can be utilized for, among many other things, creating better in vitro models of human barrier tissues, which can be used for drug screening. These membranes can be part of microfluidic systems or non-microfluidic systems. Accordingly, the membranes can be utilized, for example, to mimic three-dimensional barrier tissue such as intestinal (GI epithelium, villi), placental, lung, blood/brain barrier, and can for example be used to predict the bioavailability of drugs. When used within a microfluidic system, it is envisioned for example that the fabrication method will enable the development of multi-tissue devices that include barrier tissues such as the gastrointestinal tract and the lung epithelium that are important to simulate the uptake of a drug through inhalation and ingestion. According to an embodiment, the microporous membrane provides access and flow in both directions of the membrane of a microfluidic cell culture.

Although the present invention has been described in connection with a preferred embodiment, it should be understood that modifications, alterations, and additions can be made to the invention without departing from the scope of the invention as defined by the claims.

What is claimed is:

1. A method of producing a three-dimensional porous membrane in a microfluidic chamber, the method comprising the steps of:
    applying a photoresist material onto the microfluidic chamber to form a photoresist material layer, wherein the microfluidic chamber comprises a plurality of silicon pillars;
    exposing a peripheral portion of the photoresist material layer to radiation, wherein exposing the photoresist material layer to radiation cross-links the exposed peripheral portion to the microfluidic chamber;
    masking, using a mask comprising a plurality of pores formed therein, the photoresist material layer;
    exposing a top layer of the masked photoresist material layer to radiation to form a porous membrane layer of cross-linked photoresist material;
    removing non-exposed photoresist material from under the porous membrane layer;
    air-drying the porous membrane layer such that the porous membrane layer adopts, as it dries, a three-dimensional shape corresponding to the plurality of silicon pillars; and
    removing, via etching, the plurality of silicon pillars, wherein the air-dried porous membrane layer retains, after etching, the three-dimensional shape corresponding to the plurality of silicon pillars.

2. The method of claim 1, further comprising the step of:
    etching a portion of the microfluidic chamber to create the plurality of silicon pillars.

3. The method of claim 1, further comprising the steps of:
    applying a first polymer material onto the microfluidic chamber to form a first polymer layer.

4. The method of claim 3, further comprising the step of removing the first polymer material.

5. The method of claim 1, wherein the photoresist material is SU-8.

6. The method of claim 3, wherein the steps of applying the first polymer material onto the etched microfluidic chamber and applying the photoresist material comprise spin coating.

7. The method of claim 1, wherein the step of removing the non-exposed photoresist material from under the porous membrane layer comprises incubating in photoresist material developer.

8. The method of claim 2, wherein said etching step comprises the steps of:
    applying an initial photoresist material onto the microfluidic chamber to form an initial photoresist material layer;
    exposing the initial photoresist material layer to radiation in a predetermined pillar array pattern;
    etching the microfluidic chamber to create a plurality of silicon pillars corresponding to the predetermined pillar array pattern formed in the exposed initial photoresist material layer; and
    removing all of the initial photoresist material.

9. The method of claim 1, further comprising the steps of:
seeding the porous membrane layer with a plurality of cells; and
incubating the seeded porous membrane layer under conditions suitable to promote growth of said seeded cells.

10. The method of claim 9, wherein said plurality of cells are Caco-2 cells.

11. A method of producing a porous membrane in a microfluidic chamber, the method comprising the steps of:
applying a photoresist material onto the microfluidic chamber to form a photoresist material layer;
exposing a peripheral portion of the photoresist material layer to radiation, wherein exposing the photoresist material layer to radiation cross-links the exposed peripheral portion to the microfluidic chamber;
masking, using a mask comprising a plurality of pores formed therein, the photoresist material layer;
exposing a top layer of the masked photoresist material layer to radiation to form a porous membrane layer of cross-linked photoresist material;
removing the non-exposed photoresist material from under the porous membrane layer;
drying the porous membrane layer such that the porous membrane layer adopts, as it dries, a three-dimensional shape corresponding to the plurality of silicon pillars; and
removing, via etching, the plurality of silicon pillars, wherein the dried porous membrane layer retains the three-dimensional shape corresponding to the plurality of silicon pillars after etching.

12. The method of claim 11, wherein the photoresist material is SU-8.

13. The method of claim 11, wherein the method further comprises, prior to said masking step, the step of:
exposing a central portion of the photoresist material layer to radiation, wherein a plurality of cross-linked support posts are created in said photoresist material layer.

14. The method of claim 11, further comprising the step of:
seeding the porous membrane layer with a plurality of cells; and
incubating the seeded porous membrane layer under conditions suitable to promote growth of said seeded cells.

* * * * *